United States Patent
Higgitt et al.

(10) Patent No.: US 9,682,183 B2
(45) Date of Patent: Jun. 20, 2017

(54) DIALYSIS MACHINE

(75) Inventors: Ben Higgitt, Redditch (GB); Mark Wallace, Kinver (GB)

(73) Assignee: Quanta Fluid Solutions Ltd., Warwickshire (GB)

(*) Notice: Subject to any disclaimer, the term of this patent is extended or adjusted under 35 U.S.C. 154(b) by 483 days.

(21) Appl. No.: 14/374,769

(22) PCT Filed: Feb. 14, 2012

(86) PCT No.: PCT/GB2012/000147
§ 371 (c)(1),
(2), (4) Date: Sep. 8, 2014

(87) PCT Pub. No.: WO2013/121162
PCT Pub. Date: Aug. 22, 2013

(65) Prior Publication Data
US 2015/0129481 A1    May 14, 2015

(51) Int. Cl.
*A61M 1/16* (2006.01)

(52) U.S. Cl.
CPC ............ *A61M 1/1652* (2014.02); *A61M 1/16* (2013.01); *A61M 1/1656* (2013.01); *A61M 2202/0413* (2013.01); *A61M 2205/10* (2013.01); *A61M 2205/122* (2013.01); *F04C 2270/041* (2013.01)

(58) Field of Classification Search
CPC .... A61M 1/16; A61M 1/1652; A61M 1/1656; A61M 2202/0413; A61M 2205/10; A61M 2205/122; F04C 2270/041
See application file for complete search history.

(56) References Cited

U.S. PATENT DOCUMENTS

| | | |
|---|---|---|
| 6,261,065 B1 | 7/2001 | Nayak et al. |
| 2003/0217962 A1 | 11/2003 | Childers et al. |
| 2007/0112297 A1 | 5/2007 | Plahey et al. |
| 2009/0012455 A1 | 1/2009 | Childers et al. |
| 2011/0185722 A1 | 8/2011 | Sebesta et al. |
| 2011/0303597 A2 | 12/2011 | Gunther et al. |

OTHER PUBLICATIONS

Nov. 13, 2012 International Search Report for PCT/GB2012/000147.
Aug. 28, 2014 Transmittal of Int'l. Preliminary Report on Patentability for PCT/GB2012/000147.

*Primary Examiner* — John Kim
(74) *Attorney, Agent, or Firm* — Hahn Loeser & Parks, LLP (57) ABSTRACT

A hemodialysis machine including a main body and a door, the door being capable of opening and closing relative to the main body so as to receive and retain a disposable cartridge therebetween, the machine further including a controller and a pneumatic pump, the cartridge having a chassis with a platen side covered by a first deformable membrane and a door side covered by a second deformable membrane, the chassis and membranes defining a dialysate flow path for delivering a flow of dialysate solution through a dialyzer, the main body having a platen for in use sealing against the platen side of the cartridge and the door having an interface plate for in use sealing against the door side of the cartridge, the pneumatic pump being fluidically connected to an interface plate cavity between the interface plate and the cartridge by a pneumatic supply line, the pump being controlled by the controller to selectively generate a vacuum in the platen cavity so as to affix the cartridge to the door prior to operation of the machine.

9 Claims, 8 Drawing Sheets

DIALYSIS MACHINE

The present application is a §371 submission of international application no. PCT/GB2012/000147, which was filed on 14 Feb. 2012 and entitled Dialysis Machine, and which was published in the English language on 22 Aug. 2013 with publication no. WO 2013/121162 A1.

The present invention relates to dialysis machines and in particular, but not exclusively, to a disposable cartridge for use in hemodialysis machine.

Dialysis is a treatment which replaces the renal function of removing excess fluid and waste products, such as potassium and urea, from blood. The treatment is either employed when renal function has deteriorated to an extent that uremic syndrome becomes a threat to the body's physiology (acute renal failure) or, when a longstanding renal condition impairs the performance of the kidneys (chronic renal failure).

There are two major types of dialysis, namely hemodialysis and peritoneal dialysis.

In peritoneal dialysis treatment, a dialysate solution is run through a tube into the peritoneal cavity. The fluid is left in the cavity for a period of time in order to absorb the waste products, and is subsequently removed through the tube for disposal.

It is common for patients in the early stages of treatment for a longstanding renal condition to be treated by peritoneal dialysis before progressing to hemodialysis at a later stage.

In hemodialysis, the patient's blood is removed from the body by an arterial line, is treated by the dialysis machine, and is then returned to the body by a venous line. The machine passes the blood through a dialyser containing tubes formed from a semi permeable membrane. On the exterior of the semi permeable membrane is a dialysate solution. The semi permeable membrane filters the waste products and excess fluid from the blood into the dialysate solution. The membrane allows the waste and a controlled volume of fluid to permeate into the dialysate whilst preventing the loss of larger more desirable molecules, like blood cells and certain proteins and polypeptides.

The action of dialysis across the membrane is achieved primarily by a combination of diffusion (the migration of molecules by random motion from a region of higher concentration to a region of lower concentration), and convection (solute movement that results from bulk movement of solvent, usually in response to differences in hydrostatic pressure).

Fluid removal (otherwise known as ultrafiltration) is achieved by altering the hydrostatic pressure of the dialysate side of the membrane, causing free water to move across the membrane along the pressure gradient.

The correction of uremic acidosis of the blood is achieved by use of a bicarbonate buffer. The bicarbonate buffer also allows the correction of the blood bicarbonate level.

The dialysis solution consists of a sterilized solution of mineral ions. These ions are contained within an acid buffer which is mixed with the sterilised water and bicarbonate base prior to delivery to the dialyser.

Dialysate composition is critical to successful dialysis treatment since the level of dialytic exchange across the membrane, and thus the possibility to restore adequate body electrolytic concentrations and acid-base equilibrium, depends on the composition.

The correct composition is accomplished primarily by formulating a dialysate whose constituent concentrations are set to approximate normal values in the body.

Additionally, the balance of fluids across the dialyser is critical in providing effective treatment. Any instability in the volume of dialysate pumped into and out of the dialyser can cause a flow balance error which can lead to dehydration of over-hydration of the patient over the course of a treatment.

Achieving the correct composition of dialysate and providing accurate flow balance across the dialyser requires the accurate control of low volumes of liquid and at present this is achieved by the provision of complex fluid paths, including multiple pumping and valving components on the dialysis machine.

This adds cost and complexity to the machine and necessitates the sterilisation of the fluid paths, and pumping and valving components between treatments.

The provision of a dialysate cartridge which can be disposed of after a treatment offers a solution to this problem but presents additional technical challenges in terms of achieving an accurate composition of dialysate and the correct balance of fluids across the dialyser.

Thus it is known to provide a dialysate flowpath on a cartridge having membrane on each side of a cartridge chassis. The membranes are actuated by the machine to pump and control the dialysate fluid.

However, the positioning of the cartridge in the machine is critical to achieving accurate mixing and flow balance since any variation in position of the cartridge can lead to irregular actuation of the membrane and consequently variation in pumped fluid volume.

Furthermore any unwanted compliancy in the membrane can lead to inconsistent dialysate composition and flow balance accuracy due to volumetric variation in the fluid system.

It is an object of the present invention to provide a hemodialysis machine which at least mitigates some of the problems described above.

According to the invention there is provided a hemodialysis machine including
  a main body and a door, the door being capable of opening and closing relative to the main body so as to receive and retain a disposable cartridge therebetween,
  the machine further including a controller and a pneumatic pump,
  the cartridge having a chassis with a platen side covered by a first deformable membrane and a door side covered by a second deformable membrane, the chassis and membranes defining a dialysate flow path for delivering a flow of dialysate solution through a dialyser,
  the main body having a platen for in use sealing against the platen side of the cartridge and the door having an interface plate for in use sealing against the door side of the cartridge,
  the pneumatic pump being fluidically connected to an interface plate cavity between the interface plate and the cartridge by a pneumatic supply line, the pump being controlled by the controller to selectively generate a vacuum in the platen cavity so as to affix the cartridge to the door prior to operation of the machine.

Advantageously, the generation of a vacuum in the interface cavity causes the second deformable membrane to be drawn into contact with the interface plate. The prevents deflection of the second membrane as a result of the pressure variations observed on the inner surface of the membrane resulting from the actuation of the first membrane to pump fluid through the cartridge. This in turn ensures that the cross section of the fluid pathways, defined at least in part by the second membrane, does not vary through the course of a treatment. This ensures the accuracy of the pumping of fluid on the cartridge by reducing volumetric errors which can accumulate over the course of a treatment to adversely affect flow balance or mixing accuracy.

Preferably, the pneumatic supply line is defined at least in part by a port through the cartridge which permits the gas in the interface cavity to be exhausted from the cavity by the pump to generate a vacuum in the cavity.

Preferably, the platen defines an aperture in fluid communication with the port in the cartridge, the aperture permitting the gas in the interface cavity to be exhausted from the cavity by the pump to generate a vacuum in the cavity.

Preferably, the platen includes at least one o-ring seal situated circumferentially around the aperture in order to form a seal between the platen and the cartridge.

Preferably, the interface plate carries an interface plate gasket for holding the vacuum in the interface cavity between the interface plate and at least part of the second deformable membrane.

Preferably, the door includes an actuator operable to apply a closure load to the cartridge.

Preferably, the closure load is sufficient to cause the cartridge to engage substantially the entire interface plate gasket sealing surface.

Preferably, the actuator is a pneumatically operable airbag.

Preferably, the interface plate has a recess in its surface to allow the exhaustion of gas from the interface plate cavity.

Preferably, the recess includes a depression aligned with the port in the cartridge.

The invention will now be described, by way of example only, and with reference to the following drawings, in which.

Figure 1:
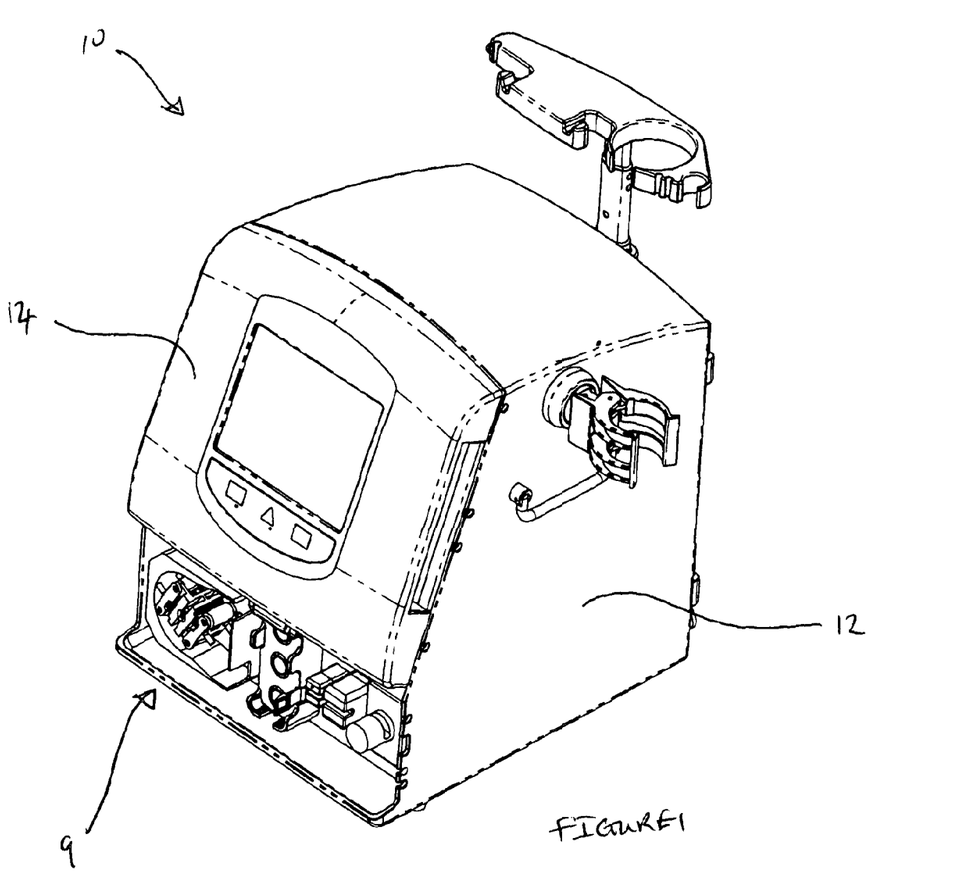
FIG. 1 is an isometric view of a dialysis machine according to the present invention.

Referring to FIG. 1, a dialysis machine 10 is shown having a main body 12 and a hinged door 14. The door 14 is hinged so as to allow a dialysis cartridge 16 (see FIG. 6) to be received between the main body 12 and the door. The machine 10 has a blood pumping portion indicated generally at 9 for pumping patient blood to and from a dialyser (not shown for clarity) in a known manner.

Figure 2:
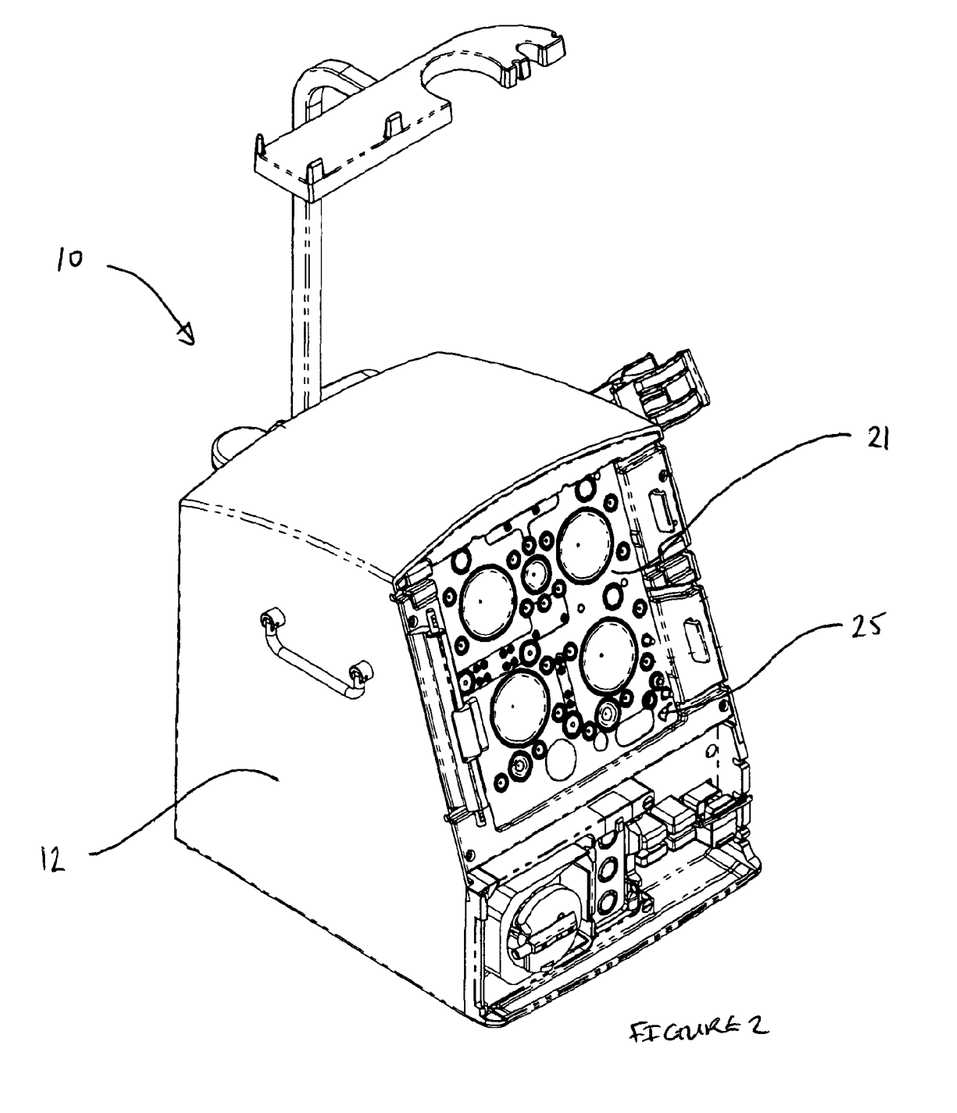
FIG. 2 is an isometric view of the machine of FIG. 1 with the door removed showing the platen.

Referring to FIG. 2, the main body 12 has a platen 21 behind which is an engine portion (not shown for clarity). The platen 21 is configured to receive the cartridge 16 within a recessed portion 25. The engine portion includes a pneumatic pump for providing pressure and vacuum to operate the machine and a controller to control retention of the cartridge 16 within the machine 10 and fluid flow on the cartridge 16 as will be discussed in further detail below.

Figure 3:
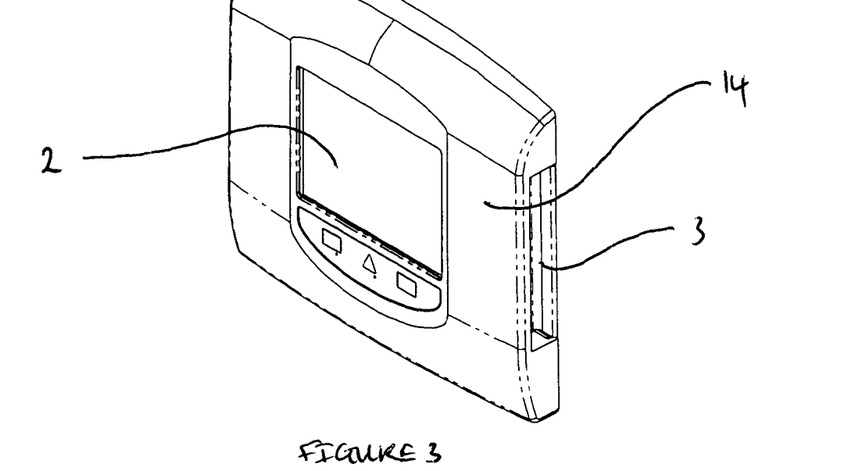
FIG. 3 is an isometric view of the outside of the door of the machine of FIG. 1.
Figure 4:
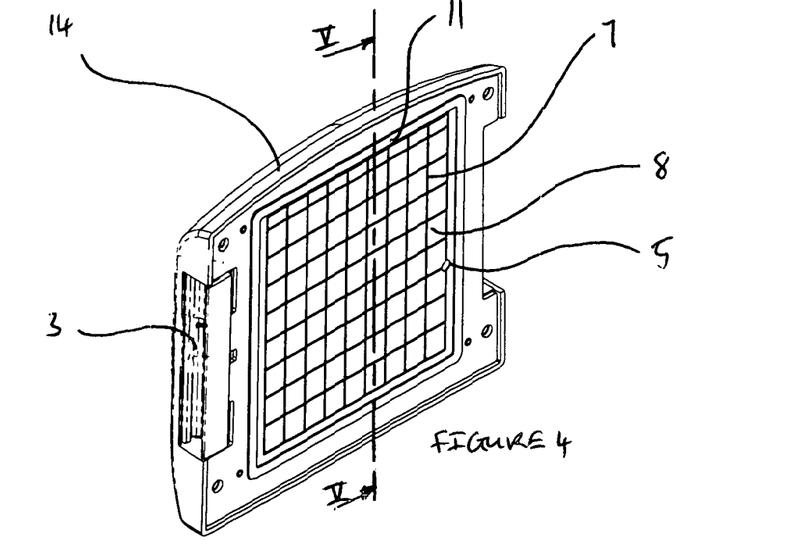
FIG. 4 is an isometric view of the inside of the door of the machine of FIG. 1.

The door 14 is shown in further detail in FIGS. 3 and 4. The door 14 has an outer side including a user interface 2, an edge defining a handle 3 for opening and closing the door and an inner side including an interface plate 8 for engaging the cartridge 16 when the door is closed. The interface plate 8 has a flat profile which defines a series of recesses 7 which, in this example, form a grid. The grid is surrounded by an interface plate gasket in the form of continuous seal 11. The recesses are recessed by approximately 0.7 mm from the surface of the interface plate 8. The recesses 7 include an access depression 5, the purpose of which will be described in further detail shortly.

Figure 5:
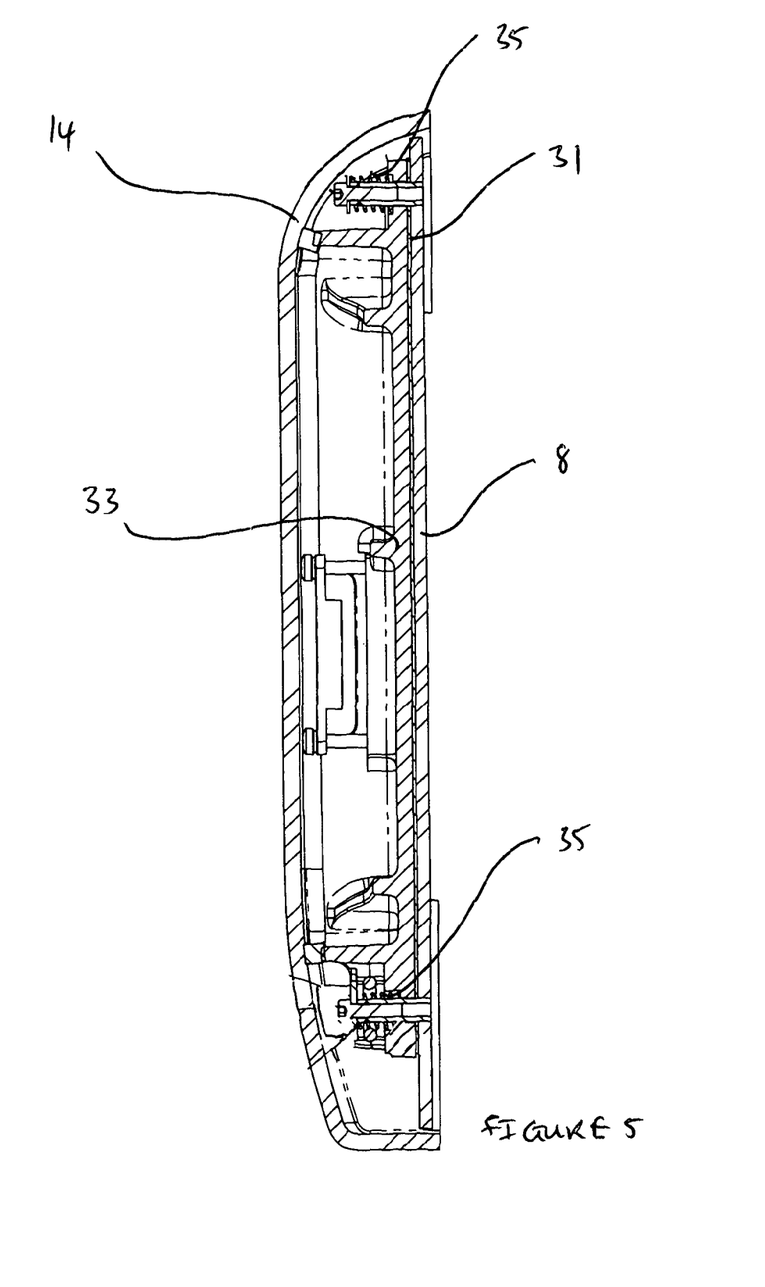
FIG. 5 is sectioned side view of the door of FIG. 4 taken along line V-V in FIG. 4.

Referring now to FIG. 5, the door 14 includes an actuator in the form of an airbag 31 situated between the interface plate 8 and a door chassis 33. The airbag 31 is operable by the engine portion to urge the interface plate 21 away from the door chassis 33 towards the main body 12 via a pneumatic line which runs through the hinge between the door 14 and the main body 12. In this way the airbag 31 provides a closure load to close the cartridge onto the platen and to ensure that the continuous seal 11 fully engages the cartridge 16. Upon deactivation of the airbag 31, the interface plate 8 returns to its original position under the action of springs 35.

The cartridge 16 will now be described in further detail with reference initially to FIG. 6. The cartridge 16 has a chassis defining a door side 20 (shown in further detail in FIG. 7) and a platen side 18 (shown in further detail in FIG. 8). In use the platen side 18 of the cartridge 16 engages the platen 21 on the main body 12 of the machine 10, and the door side 20 engages the interface plate 8 on the door 14 of the machine 10. The cartridge has a vacuum passage port 23 which is open on both sides of the cartridge 16, the purpose of which will be described in further detail below.

The cartridge 16 is formed from an acrylic such as SG-10 which is moulded in two parts (a platen side and a patient side) before being bonded together to form the chassis. Both the platen side 18 and door side 20 are covered in a clear flexible membrane 13 formed from, for example, DEHP-free PVC which is operable by pneumatic pressure applied to the membrane by the pneumatic compressor in the main body via the platen 21. In this way a series of flow paths are formed in the cartridge for carrying dialysate and its constituent parts of water, bicarbonate solution and acid solution.

In use the engine portion of the machine 10 applies either a positive or negative pressure to the membrane via the platen 21 in order to selectively open and close valves and pumps to pump fluid through the cartridge. The fluid flow through the cartridge will now be described in detail.

Figure 6:
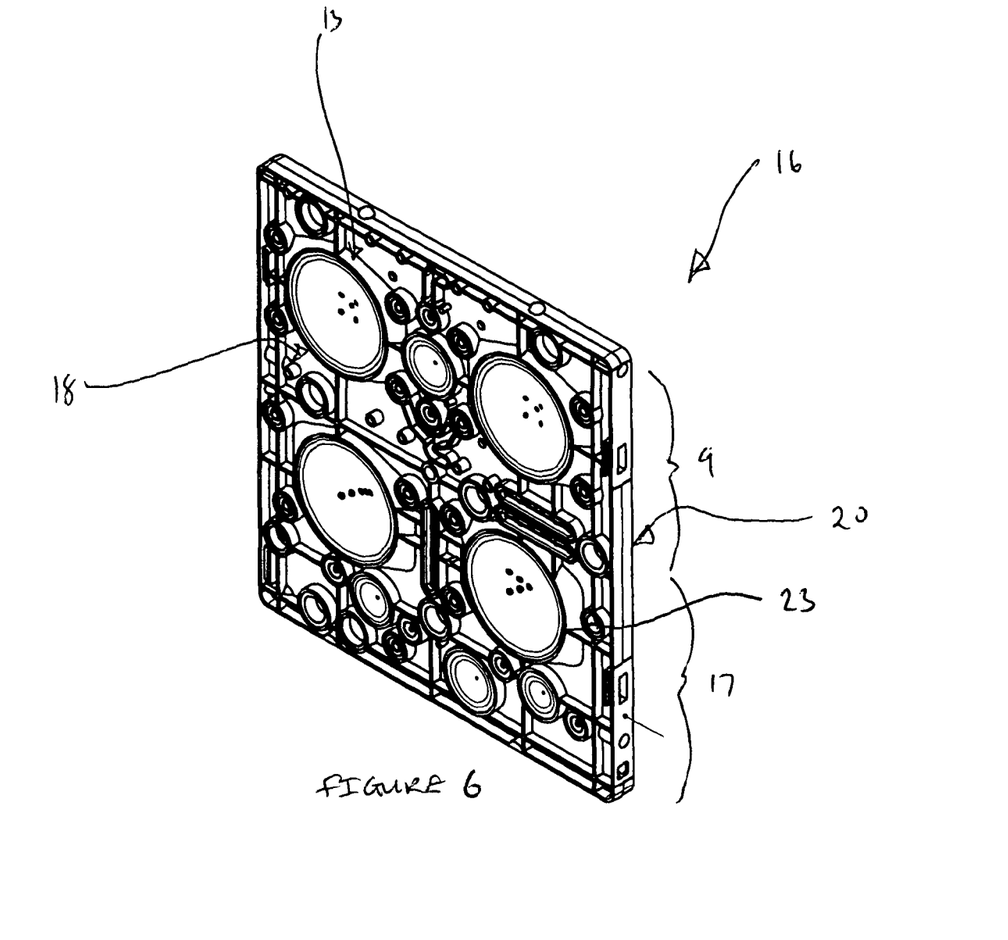
FIG. 6 is an isometric view of a cartridge for use in the machine of FIG. 1.

The cartridge 16 has a dialysate mixing portion indicated generally at 17 in FIG. 6 and a flow balancer indicated generally at 19 in FIG. 6. The purpose of the mixing portion is to deliver accurately mixed homogeneous dialysate solution to the flow balancer which is provided to ensure that the flow of fluid supplied to the dialyser matches (to within clinical tolerances) the volume of fluid drawn from the dialyser.

Dialysate Mixing

Dialysate is mixed on the cartridge by combining water with two dialysate base solutions, namely a bicarbonate solution and an acid solution. This process will now be described in further detail.

Figure 7:
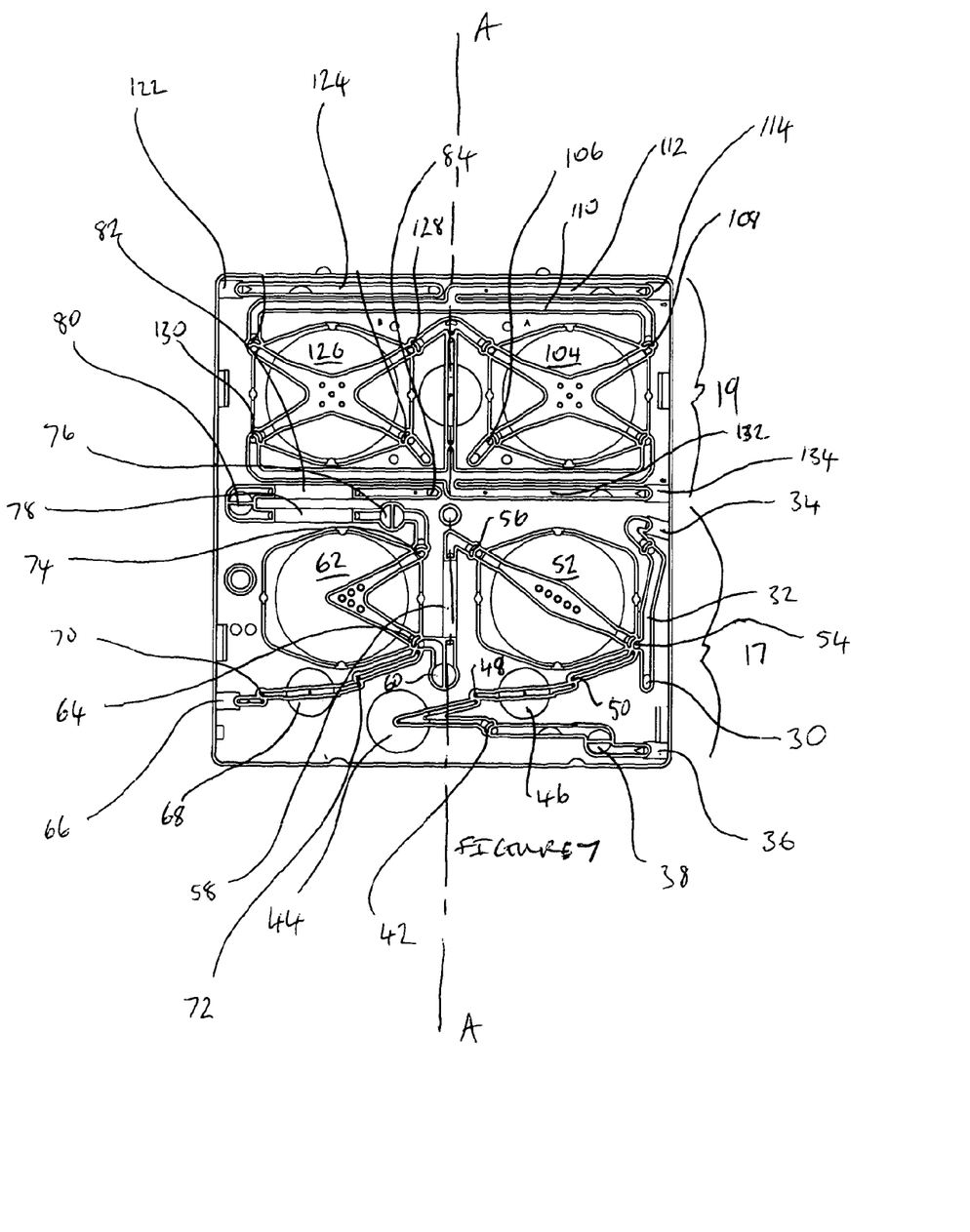
FIG. 7 is a plan view of the door side of the cartridge of FIG. 6.
Figure 8:
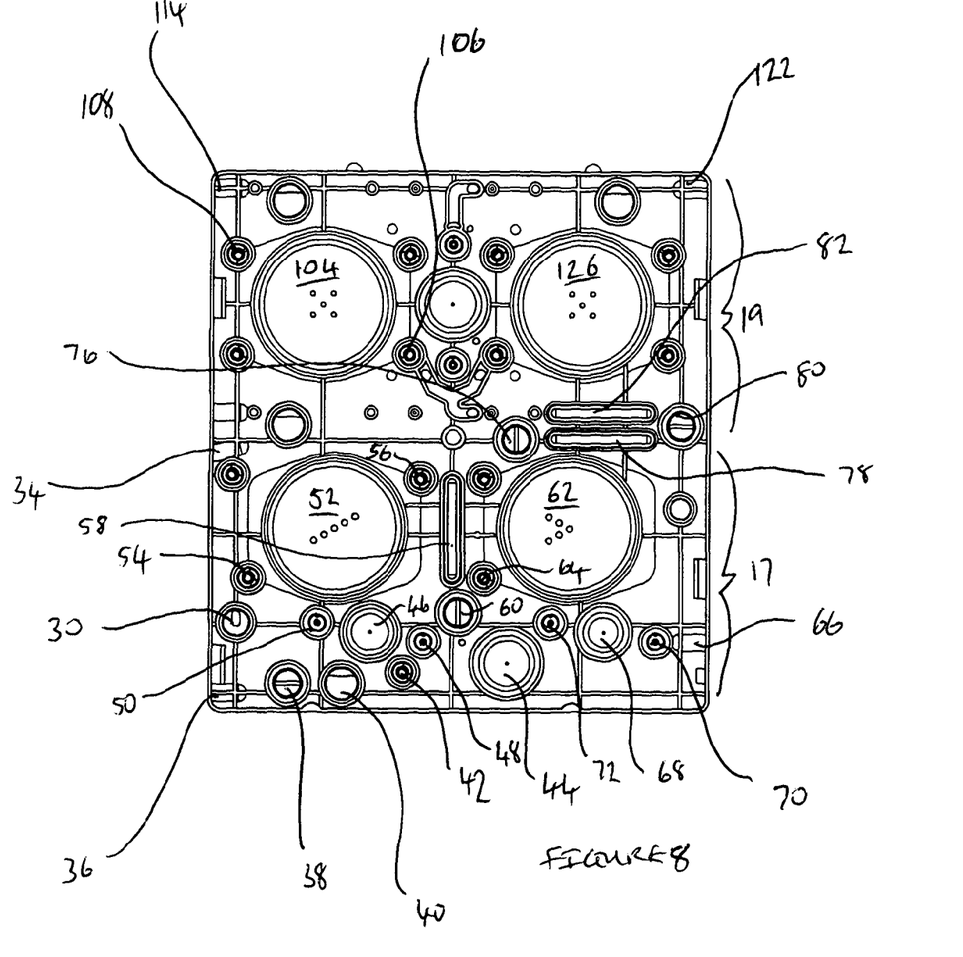
FIG. 8 is a plan view of the platen side of the cartridge of FIG. 6.

Referring now to FIGS. 7 and 8, dialysate solution is mixed in the mixing portion 17 of the cartridge 16 as follows. Reverse osmosis (RO) water is admitted onto the cartridge via RO water inlet port 30. Water passes up channel 32 and exits the cartridge 16 at RO water outlet port 34. From here the water is carried via a tube (not shown for clarity) and passes through a bicarbonate cartridge in a known manner to generate a bicarbonate solution. The bicarbonate solution is admitted onto the cartridge 16 via bicarbonate inlet port 36. The temperature of the bicarbonate solution is measured at sensing port 38 and the bicarbonate solution pressure is measured at sensing port 40 (FIG. 8 only). The bicarbonate solution passes a bicarbonate control valve 42 before entering a bicarbonate solution reservoir 44. A first dialysate base solution pump chamber in the form of a bicarbonate dosing pump chamber 46 has an associated inlet valve 48 and outlet valve 50. From the outlet valve 50 the bicarbonate solution passes to a first mixing pump chamber in the form of a bicarbonate pump chamber 52 via bicarbonate pump inlet valve 54. The bicarbonate pump inlet valve 54 also admits RO water into the bicarbonate pump chamber 52 from the RO water inlet port 30. In this way RO water and bicarbonate solution can be admitted into the bicarbonate pump chamber 52 for subsequent pumping out of the bicarbonate pump chamber 52 of a mixed bicarbonate and water solution (called bicarbonate mixture from hereon in for ease of reference) via a bicarbonate pump outlet valve 56. From the bicarbonate pump outlet valve 56 the bicarbonate mixture enters a bicarbonate mixture sensor channel 58 in which the machine 12 measures the conductivity of the mixture in a known manner. The mixture then enters a bicarbonate mixture temperature sensor 60 before entering a second mixing pump chamber in the form of an acid pump chamber 62 via acid pump inlet valve 64. Also admitted into the acid pump chamber 62 is an acid solution which enters the cartridge from a known bagged supply (not shown for clarity) at an acid solution inlet port 66. From the acid inlet port 66 the acid solution passes through a second dialysate base solution pump chamber in the form of an acid dosing pump chamber 68 via acid dosing pump chamber inlet valve 70 and an outlet valve 72. In this way bicarbonate mixture and acid solution are admitted into the acid pump chamber 62 for subsequent pumping out of the pump chamber 62 of a fully mixed dialysate solution via an acid pump outlet valve 74. From here the fully mixed dialysate solution passes through a first dialysate temperature sensor 76 and first dialysate conductivity sensor 78. A second dialysate temperature sensor 80 and second dialysate conductivity sensor 82 are provided to corroborate the data provided by the first sensors 76, 78.

Fully mixed dialysate solution then passes through aperture 84 (shown in FIG. 7 only) to be received by the flow balance portion 19 of the cartridge 16.

Flow Balance

The flow balancer 19 is mirrored about centreline A-A as shown in FIG. 7. The flow balancer 19 will be described with reference to FIGS. 7 and 8.

Dialysate solution passes from the aperture 84 into the first flow balance pump chamber 104 through inlet valve 106 upon the actuation of the membrane by the machine 10 to draw the dialysate into the pump chamber of pump 104. The dialysate solution is then pumped out of the pump chamber 104 via outlet valve 108 upon the closure of the inlet valve 106. The dialysate solution then passes down a channel 110 before passing into a dialyser outlet channel 112. From there the dialysate solution exits the cartridge via dialyser outlet 114 and is carried to a dialyser (not shown for clarity).

The dialysate solution returns to the cartridge from the dialyser via a tubing set (also not shown for clarity). A second flow balance pump chamber 126 is actuated to draw the dialysate solution through the inlet 122, down dialyser inlet channel 124, passed the second flow balance pump inlet valve 128 and into the pump chamber 126. The dialysate solution is then pumped out of the pump chamber 126 via an outlet valve 130 upon the closure of the inlet valve 128. The dialysate solution then passes down a drain outlet channel 132. From there the dialysate solution exits the cartridge via drain outlet 134 and is carried to a drain (not shown for clarity).

The operation of the first and second flow balance pumps can be switched by virtue of the mirroring of the valves and pump chambers. In this way the first flow balance pump 104 is also used to draw dialysate solution form the dialyser 118 and the second flow balance pump 126 is used to pump dialysate solution into the dialyser 118. This allows the pumps to switch over the course of a treatment ensuring that any geometric variance between the first and second pump chambers is balanced out.

Control of Dialysate Mixing

In use the volume of bicarbonate and acid solution mixed with the RO water must be closely monitored and controlled in order to achieve effective treatment. The monitoring is achieved in a known manner using conductivity sensors 78, 82 (see FIG. 7). In the present invention the conductivity signal generated by these sensors (which is indicative of the strength of the admixture) is used to control the volume of bicarbonate solution pumped through the bicarbonate dosing pump chamber 46 into the bicarbonate pump chamber 52 and the volume of acid solution pumped through the acid dosing pump chamber 68 into the acid pump chamber 62 as follows.

Figure 9:
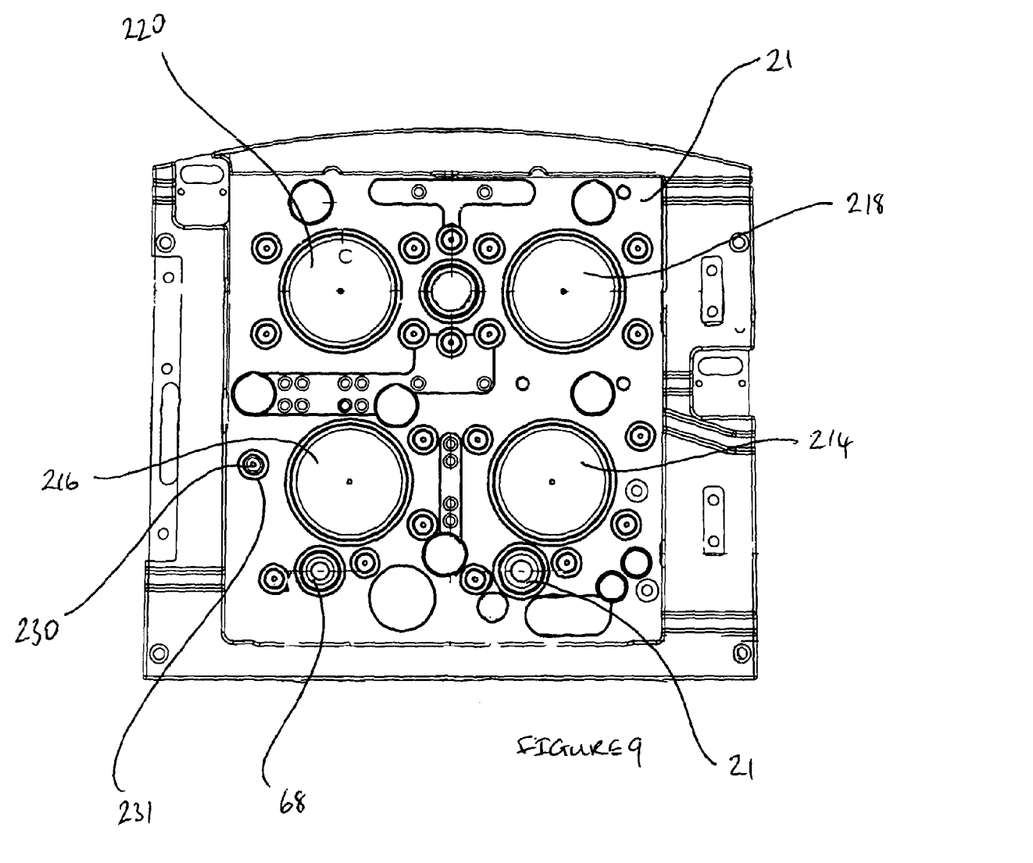
FIG. 9 is a plan view of the platen of the machine of FIG. 1.

Referring to FIG. 9 the platen 21 has features which correspond to the features on the cartridge 16. The platen 21 has the following features:

- a first dialysate base solution pump cavity in the form of bicarbonate dosing pump cavity 210 which corresponds to the bicarbonate dosing pump chamber 46 on the cartridge 16 and which together form a first dialysate base solution pump;
- a second dialysate base solution pump cavity in the form of an acid dosing pump cavity 212 which corresponds to the acid dosing pump chamber 68 on the cartridge 16 which together form a first dialysate base solution pump;
- a first mixing pump cavity in the form of a bicarbonate pump cavity 214 which corresponds to the bicarbonate pump chamber 52 on the cartridge 16 which together form a first mixing pump;
- a second mixing pump cavity in the form of an acid pump cavity 216 which corresponds to the acid pump chamber 62 on the cartridge 16 which together form a second mixing pump;
- a first flow balance pump cavity 218 which corresponds to the first flow balance pump chamber 104 on the cartridge 16 which together form a first flow balance pump; and
- a second flow balance pump cavity 220 which corresponds to the second flow balance pump chamber 126 on the cartridge 16 which together form a second flow balance pump.

Vacuum Attachment

The platen 21 has an aperture in the form of vacuum attachment port 230 surrounded by an o-ring seal 231. In use the vacuum passage port 23 on the cartridge 16 aligns with the vacuum attachment port 230. Similarly the access depression 5 on the interface plate 8 aligns with the vacuum passage port 23 on the door side of the cartridge 16 to form a pneumatic supply line between the engine portion and the interface plate 8.

In use the door 14 is opened by the user and the cartridge 16 inserted into the recess 25 in the platen 21. The door 14 is then closed. A load is then applied to the rear of the interface plate 8 by the airbag 31 in the door 14 in order for the cartridge to engage the gasket seal 11 on the interface place. This forms an interface cavity between the interface plate and the cartridge 16. The engine portion then applies a vacuum to the interface cavity via the pneumatic supply line (the recess 7, the access depression 5, the vacuum passage port 23 through the cartridge 16, and the vacuum attachment port 230). Under the action of the vacuum air is drawn from the recess 7 via the depression 5 which acts to ease the removal of air from the recess 7. This evacuation of air has the effect of pulling the membrane 13 on the door side of the cartridge 16 against the interface plate 8. This in turn reduces the compliancy in the membrane 13 by overcoming any pressure fluctuation observed by the membrane 13 on the door side of the cartridge 16 caused by operation of the membrane on the body side of the cartridge to pump fluid through the cartridge. This reduction in compliancy is achieved by reducing the tendency of the membrane to move under operation of the cartridge to mix and pump dialysate. This increases the volumetric accuracy of the mixing and pumping which leads to improved accuracy of dialysate composition and flow balance.

It will be appreciated that the pattern of the recesses 7 formed in the interface plate 8 is given by way of example only and that the configuration of the recesses could be changed without departure from the invention.

The invention claimed is:

1. A hemodialysis machine including
a main body and a door, the door being capable of opening and closing relative to the main body so as to receive and retain a disposable cartridge therebetween,
the machine further including a controller and a pneumatic pump,
the cartridge having a chassis with a platen side covered by a first deformable membrane and a door side covered by a second deformable membrane, the chassis and membranes defining a dialysate flow path for delivering a flow of dialysate solution through a dialyser,
the main body having a platen for in use sealing against the platen side of the cartridge and the door having an interface plate for in use sealing against the door side of the cartridge,
the pneumatic pump being fluidically connected to an interface plate cavity between the interface plate and the cartridge by a pneumatic supply line, the pump being controlled by the controller to selectively generate a vacuum in the interface plate cavity so as to affix the cartridge to the door prior to operation of the machine;
wherein the pneumatic supply line is defined at least in part by a port through the cartridge which permits the gas in the interface cavity to be exhausted from the cavity by the pump to generate a vacuum in the cavity.

2. The machine according to claim 1 wherein the platen defines an aperture in fluid communication with the port in the cartridge, the aperture permitting the gas in the interface cavity to be exhausted from the cavity by the pump to generate a vacuum in the cavity.

3. The machine according to claim 2 wherein the platen includes at least one o-ring seal situated circumferentially around the aperture in order to form a seal between the platen and the cartridge.

4. The machine according to claim 1 wherein the interface plate carries an interface plate gasket for holding the vacuum in the interface cavity between the interface plate and at least part of the second deformable membrane.

5. The machine according to claim 1 wherein the door includes an actuator operable to apply a closure load to the cartridge.

6. The machine according to claim 4
wherein the door includes an actuator operable to apply a closure load to the cartridge; and
wherein the closure load is sufficient to cause the cartridge to engage substantially the entire interface plate gasket sealing surface.

7. The machine according to claim 5 wherein the actuator is a pneumatically operable airbag.

8. The machine according claim 1 wherein the interface plate has a recess in its surface to allow the exhaustion of gas from the interface plate cavity.

9. The machine according to claim 8 wherein the recess includes a depression aligned with the port in the cartridge.

* * * * *